United States Patent
Yates et al.

(10) Patent No.: US 12,062,298 B2
(45) Date of Patent: Aug. 13, 2024

(54) EYE MODEL FOR WIDE FIELD FUNDUS IMAGING

(71) Applicant: Retivue, LLC, Charlottesville, VA (US)

(72) Inventors: Paul A. Yates, Charlottesville, VA (US); Ming Lai, Pleasanton, CA (US); Ta-Wei Yi, Pleasanton, CA (US)

(73) Assignee: RetiVue, LLC, Charlottesville, VA (US)

( * ) Notice: Subject to any disclaimer, the term of this patent is extended or adjusted under 35 U.S.C. 154(b) by 509 days.

(21) Appl. No.: 16/325,781

(22) PCT Filed: Aug. 16, 2017

(86) PCT No.: PCT/US2017/047169
§ 371 (c)(1),
(2) Date: Feb. 15, 2019

(87) PCT Pub. No.: WO2018/035239
PCT Pub. Date: Feb. 22, 2018

(65) Prior Publication Data
US 2019/0213917 A1    Jul. 11, 2019

Related U.S. Application Data

(60) Provisional application No. 62/375,547, filed on Aug. 16, 2016.

(51) Int. Cl.
*G09B 23/30* (2006.01)
*A61B 3/14* (2006.01)
*A61B 3/117* (2006.01)

(52) U.S. Cl.
CPC ............... *G09B 23/30* (2013.01); *A61B 3/14* (2013.01); *A61B 3/1173* (2013.01)

(58) Field of Classification Search
CPC ...... G09B 23/303; G09B 23/30; G09B 23/26; G09B 23/28; A61B 3/14; A61B 3/10;
(Continued)

(56) References Cited

U.S. PATENT DOCUMENTS 5,221,208 A    6/1993   Alexander
5,460,646 A    10/1995  Lazzouni et al.
(Continued)

FOREIGN PATENT DOCUMENTS

WO    WO-2010084595 A1 *  7/2010  ............. G09B 23/34
WO       2016040935          3/2016

OTHER PUBLICATIONS

English translation of WO 2010084595, machine translated on Feb. 25, 2022. (Year: 2010).*
(Continued)

*Primary Examiner* — Jie Lei
(74) *Attorney, Agent, or Firm* — Simpson & Simpson, PLLC

(57) ABSTRACT

The present invention contemplates an infant eye model for wide field retinal imaging by implementing nominal physical parameters and optical characteristics found in scientific literature and by simulating retinal features and details found in real eye images. The present invention also contemplates implementing a corneal model with a translucent plastic to mimic image haze and $1^{st}$ Purkinje reflection. The present invention also contemplates implementing a birefringent layer to the lens posterior surface to simulate $4^{th}$ Purkinje reflection and its brightness variation. The present invention further contemplates implementing a photo-realistic retinal hemisphere shell to provide retinal details and demonstrate retinopathy associated with retinal diseases.

17 Claims, 3 Drawing Sheets

(58) Field of Classification Search
CPC ..... A61B 3/12; A61B 3/1173; A61B 3/00; A61B 3/30025; G09G 23/30; G09G 23/303; G09G 23/34; G09G 23/26; G09G 23/28; G09G 23/286
USPC ....... 351/206, 246, 205, 200, 203, 221, 211; 434/268, 262, 271, 267
See application file for complete search history.

(56) References Cited

U.S. PATENT DOCUMENTS

| | | |
|---|---|---|
| 6,485,142 B1 | 11/2002 | Sheehy et al. |
| 8,511,821 B2 * | 8/2013 | Schmid .................. G09B 23/30 351/205 |
| 2004/0189934 A1 | 9/2004 | Niven |
| 2007/0042142 A1 | 2/2007 | O'Brien et al. |
| 2013/0030524 A1 | 1/2013 | Akura et al. |
| 2014/0043398 A1 | 2/2014 | Butler et al. |
| 2014/0356836 A1 | 12/2014 | Van Dalen et al. |

OTHER PUBLICATIONS

Learning Resources, "Learning Resources Cross-Section Eye Model", Amazon, Jun. 26, 2015 (https://www.amazon.in/Learning-Resources-Cross-Section-Eye-Model/dp/B0012OI6DG). (Year: 2015).*

Notification of Transmittal, International Search Report, and Written Opinion for International Application No. PCT/US17/47169; International Filing Date Aug. 16, 2017; date of mailing Dec. 26, 2017; 14 pages.

Ocular Imaging Eye Model, Bracket & Spanner, Ocular Instruments, Aug. 22, 2017.

* cited by examiner

EYE MODEL FOR WIDE FIELD FUNDUS IMAGING

REFERENCE TO RELATED APPLICATION

This application is a U.S. National Stage filing of International Application PCT/US2017/047169, filed Aug. 16, 2017, which claims benefit of priority of U.S. Provisional Patent Application No. 62/375,547, Yates et al., titled "Eye Model for Wide Field Fundus Imaging," filed on Aug. 16, 2016, each of which is hereby incorporated by reference herein in its entirety.

STATEMENT REGARDING FEDERALLY SPONSORED RESEARCH

This invention was made with government support under Contract No. R44 EY023505 and R44 EY028484 both awarded by the National Institute of Health. The United States Government has certain rights in the invention.

TECHNICAL FIELD

The present subject matter relates to an eye model for wide field fundus imaging. In particular, the present subject matter relates to an eye model with a photo-realistic retina for wide field fundus imaging.

BACKGROUND

A model of the human eye is used for many ophthalmic applications, including training of eye care providers, educating patients, or simulating mechanical and optical properties of the human eye for testing, development, and demonstration of ophthalmic devices. These eye models are typically simplified from the human eye in physical structure, in optical characteristics, and in retinal details to meet specific needs of these specific applications. For instance, an imaging eye model from Ocular Instrument of Bellevue, Washington, provides some of the optical characteristics that simulate some aspects of observing and imaging the human retina. However, simplifications in said eye models can alter the optical properties such that light reflections from these models do not completely replicate those characteristically seen in the human eye. In particular, when light is shone at said eye models, reflected light size, shape, brightness, location in the x,y, and z axis relative to the incident light, scattering, haze, and polarization do not fully mimic the human eye. Given that these reflections can obscure observation of the human retina, the eye model may not fully encompass the difficulty of human ocular examination. Similarly, simplification in the structure of the retina of said eye models may lack curvatures or photorealistic details of the human eye. Inaccuracies in retinal curvature or anterior eye model structures can compromise simulation in observing the peripheral retina of a human eye. Inaccuracies in retinal detail, such as representing retinal blood vessels by thread or painted illustrations using red lines, can compromise photorealism in simulating observation of retinal detail in a human eye.

Wide field retinal imaging is being used more commonly to diagnose peripheral retinal disease including diagnosis of retinopathy of prematurity and for detecting early stages of diabetic retinopathy. Wide field retinal imagers such as the Retcam from Natus Corporation of Pleasanton, California, can be used to observe and to image from edge to edge (ora serata to ora serata) of the retina to detect retinal details.

When imaging with these wide field cameras, obscuration of retinal detail from reflected and scattered light from the human eye is common and can prevent accurate diagnosis. Difficulty in retinal visualization is also made difficult by the limited retinal reflectivity of more highly pigmented eyes. Thus, diagnosing retinopathy of prematurity through wide field imaging may require a substantial amount of training and practice to position the camera relative to the human eye so as to obtain best quality images that maximize observation of retinal detail and minimize scattered and reflected light from other ocular structures of the eye. Commercially available eye models simplify ocular structure in a manner that does not allow them to accurately simulate the task of wide-field imaging on a human eye. As a result, users may find it highly desirable to have an imaging eye model that provides precise physical structure, accurate optical characteristics, accurate reflected and scattered light, and detailed retinal features and reflectivity to simulate an infant's eye and to facilitate training and practice on diagnosis with wide field fundus imaging.

SUMMARY OF THE INVENTION

Therefore, the present invention contemplates an eye model for wide field retinal imaging by implementing nominal physical parameters and optical characteristics of a human infant or adult eye and by simulating retinal features and details found in real human eye images taken by said wide-field imaging systems. The present invention also contemplates implementing a corneal model with a translucent plastic to mimic image haze and $1^{st}$ Purkinje reflection (i.e. reflection from the anterior corneal surface) as seen in a human eye. The present invention also contemplates implementing a birefringent layer to the lens posterior surface to simulate $4^{th}$ Purkinje reflection (i.e. reflection from the posterior lens surface) and its brightness variation under polarized light as seen in a human eye. The present invention further contemplates implementing a photo-realistic retinal curved shell to accurately simulate the curved surface and retinal details and retinopathy findings as seen in human eyes. Photo-realism is provided for by using a wide-field retinal photo of a human eye or composite of human eye retinal photos or composite of human eye retinal photos with additional illustration that are transferred to said retinal curved shell.

DETAILED DESCRIPTION

Figure 1:
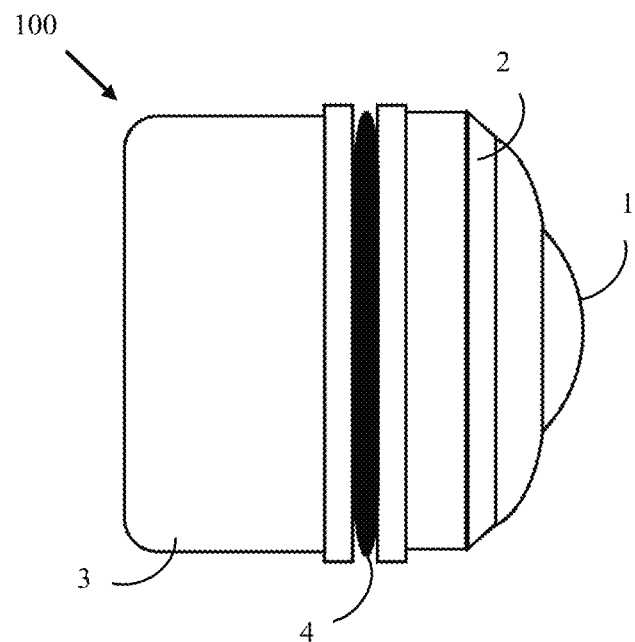
FIG. 1 illustrates an infant eye model for wide field retinal imaging.

FIG. 1 illustrates an infant eye model 100 for wide field retinal imaging. The external view of the infant eye model 100 includes a corneal model 1, a front part 2, a back part 3, and an O-ring 4.

In a preferable embodiment, the anterior surface of corneal model 1 has a nominal radius approximately 6 mm, and the outer diameter of the eye model 100 has a nominal value approximately 18 mm. The corneal model 1 is affixed to the front part 2 of the eye model 100. An O-ring 4 is to make a water tight seal between the front part 2 and the back part 3.

Figure 2:
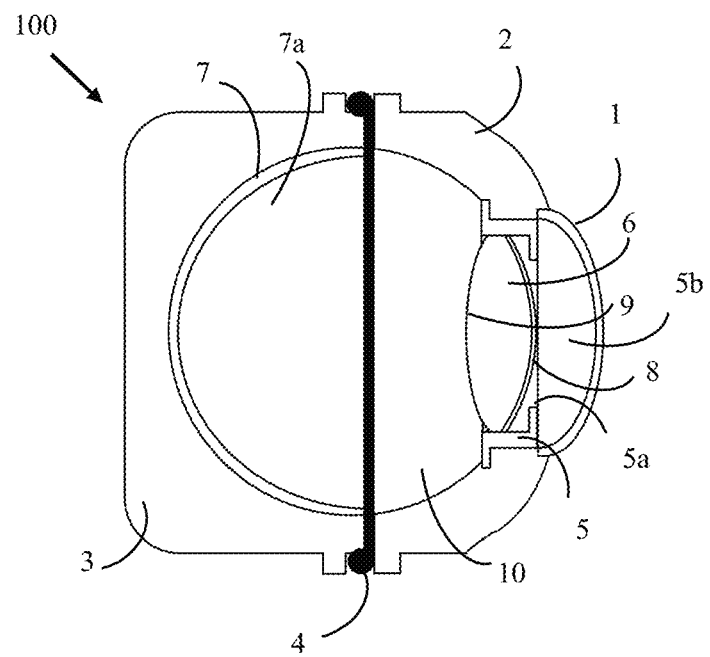
FIG. 2 illustrates a cross section of the infant eye model for wide field retinal imaging.

FIG. 2 illustrates a cross section of the infant eye model 100 for wide field retinal imaging. The cross section of the infant eye model 100 includes a corneal model 1, an iris model 5, a lens model 6, a front part 2, a back part 3, an O-ring 4, a photo-realistic retinal shell 7, and a thin birefringent layer 8.

In a preferable embodiment, the corneal model 1 has a convex anterior surface that is made to provide an anatomically accurate $1^{st}$ Purkinje reflection (i.e., the reflection from the anterior corneal surface) found as found in a human eye. In one embodiment anatomically accurate is specified by the $1^{st}$ Purkinje reflection having a characteristic position, size, shape, polarization, sharpness, scattering, and brightness as seen on a human eye. These characteristic parameters are determined for said corneal model by choice of materials, thickness of said materials, radius of curvature of said materials, diameter of said materials, and axial location of said materials in said model eye relative to other model eye anatomic structures. In one embodiment the corneal model 1 is made of a slightly translucent plastic (e.g., ACRYLITE LED from Evonik Cyro of Parsippany, New Jersey) with radius of curvature 8 mm and diameter of 13 mm to provide a $1^{st}$ Purkinje reflection of similar size, shape, position, brightness, and diffuseness as found on an adult human eye. In one embodiment the translucent plastic provides at least 10 percent scattering of incident light within the visible spectrum to mimic light scattering by the human cornea.

In a preferable embodiment, the lens model 6 is a convex-convex lens with the posterior surface 9 faster (having higher refractive power) than the anterior surface that is made to provide an anatomically accurate $4^{th}$ Purkinje reflection. In one embodiment anatomically accurate is specified by the $4^{th}$ Purkinje reflection having a characteristic position, size, shape, polarization, sharpness, scattering, and brightness as seen on a human eye. These characteristic parameters are determined for said lens model by choice of materials, thickness of said materials, anterior and posterior radius of curvature of said materials, diameter of said materials, and axial location of said materials in said model eye relative to other model eye anatomic structures. In one embodiment, the lens model 6 may be made of glass or plastic. In a preferred embodiment, slightly translucent plastic may be used for lens model 6 to better mimic the scattering haze of the human lens. In one embodiment, the posterior surface 9 of the lens model 6 has a nominal radius of 5.5 mm to provide a $4^{th}$ Purkinje reflection (i.e. reflection from the posterior lens surface) of similar position and size as found on an adult human eye. In one embodiment, a thin birefringent layer 8 can be placed on the anterior surface of said lens model to provide birefringence effects as found in the human lens. In one embodiment, the birefringent layer 8 can be made of a thin plastic sheet affixed on the anterior surface to provide at least a 15-degree retardation of polarized light.

In one embodiment, the corneal and lens model is comprised as a single integrated element. This element is defined as one having the optical and refractive characteristics of the combination of the separate corneal model and the lens model. The optical and refractive characteristics of said single integrated element can be validated as compared to the separate corneal and lens model using an optical design software such as Zemax.

The iris model 5 has an aperture 5a to define a pupil of 6 mm, a nominal size of dilated infant pupil. The iris model 5 is made of soft plastic and is used to form a water tight anterior chamber 5b with the lens model 6 and the corneal model 1. The water tight anterior chamber 5b is to be filled with water or clear mineral oil.

The front part 2 and back part 3 form an internal spherical chamber 10 for the retinal shell 7 and an external enclosure for the eye model 100. The inner spherical chamber 10 is to be filled with water or clear mineral oil.

The retinal shell 7 can be made of thermal-formable plastic and has a photo-realistic print of the retinal image on the inner wall 7a. In one embodiment, the thermal formable plastic is comprised of a thin sheet of polyvinyl chloride. In another embodiment, the thermal formable plastic is comprised of a thin sheet of polystyrene. The thermal-formable plastic may inherently allow transfer of said photo-realistic print to said plastic. The thermal-formable plastic may also have a thin coating bonded to the plastic that provides a surface that more readily allows transfer of said photo-realistic print to said plastic.

In one embodiment, a photo-realistic retinal shell is comprised in part by transfer of an image of the human retina acquired by an ophthalmic camera to the retinal shell. In one embodiment the image of the human retina comprises a wide-field image, i.e. an image covering at least 80 degree field of view relative to the central axis of the human eye. In another embodiment a photo-realistic retinal shell is comprised in part by transfer of a composite of multiple images of human retinae acquired by an ophthalmic camera to the retinal shell. This can be accomplished in one embodiment by digitally montaging one or more said plurality of said images of said human retina in a photo-editing program such as Photoshop. In another embodiment, a photo-realistic retinal shell is comprised in part by transfer of a composite of multiple images of human retinae acquired by an ophthalmic camera to the retinal shell with additional illustration on said multiple images. This can be accomplished in one embodiment by digitally montaging one or more said plurality of said images of said human retina in a photo-editing program such as Photoshop and then digitally drawing on said image in a photo-illustration program such as Adobe Illustrator or Photoshop.

The retinal image on said retinal shell is necessarily distorted during the deformation of the thermal-formable material. The retinal image prior to printing can be distorted in both horizontal and vertical axes using a photo-editing program such as Photoshop. The digital distortion within Photoshop would be performed in a direction opposite to that which occurs during deformation of the thermal-formable material such that the image on the retinal shell would have correct proportions as the human retina.

The wide-field photo-realistic image may include features of a healthy retina or a disease retina. In one embodiment, the photo-realistic image demonstrates features of retinopathy of prematurity in the peripheral aspect of the image including one or more of retinal hemorrhages, a ridge, neovascularization, and tortuous vessels. In another embodiment, the photo-realistic image demonstrates features of diabetic retinopathy including one or more of retinal hemorrhages, retinal exudate, and retinal neovascularization.

The image can be transferred to said thermal-formable material by any number of printing methods. In one embodiment, a high-resolution inkjet printer such as a Hewlett Packard Deskjet is used to print said photo-realistic image on said thermal-formable material prior to formation of the retinal shell. The resolution should be at least 600×600 dpi to prevent pixelation of the image when the retinal image is viewed within the model eye. If the eye model is to be filled with a liquid such as water the ink used in the inkjet printer can either be non-water soluble, such a pigment based inks, or the retinal shell can be coated with a water-impermeable substrate, such as lacquer, to protect said ink on said retinal shell from said liquid. In one embodiment, the ink may be able to reflect infrared light to allow viewing of the retinal image under infrared light. In one embodiment this ink is XNiteHP60-IR ink (Maxmax.com)

The shell constitutes a curved surface with the shape of the shell rotationally symmetric, and having an angular extent of at least 80 degrees relative to the optical axis of the lens model. In some embodiments, it has a spherical shape. In some embodiments, it's a hemisphere. In one embodiment, the photo-realistic retinal shell 7 has a hemispherical shape with a nominal radius of 7.5 mm.

The shell can be formed by deformation of said thermal-formable material into a curved surface. This is accomplished by heating said thermal-formable material until it becomes pliable and then deforming said thermal-formable material into the desired curved shape. In one embodiment, said deformation is accomplished by heating said thermal-formable material and then subsequently vacuum forming said thermal-formable material around a hemisphere having a diameter equal to that of a human eye.

The field of view of the retinal image may refer to the centre of the spherical retinal surface. With such a definition, the peripheral edge of the retinal hemisphere corresponds to a 180-degree field of view. The eye model 100 is constructed to mimic edge to edge detection of retinopathy of prematurity, and thus it requires a viewable field of view 160-degree or greater.

Figure 3:
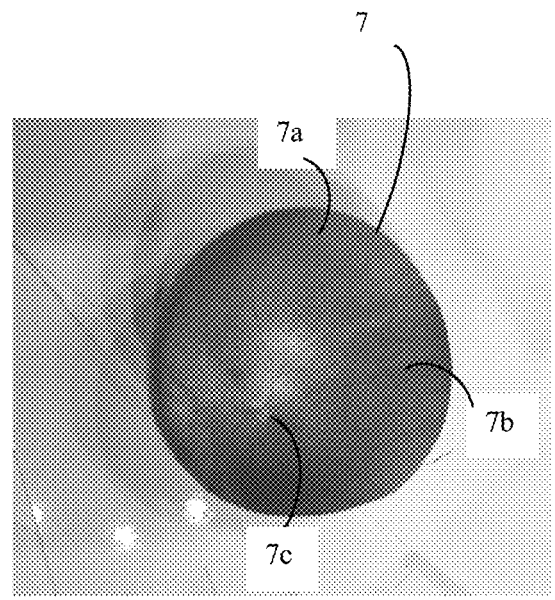
FIG. 3 illustrates a photo-realistic retinal shell of an eye model for wide field retinal imaging.

FIG. 3 illustrates a photo-realistic retinal shell 7 of an eye model for wide field retinal imaging. The inner wall 7a of the photo-realistic retinal shell 7 display high-resolution retinal features 7b including an optic disk 7c.

In a preferable embodiment, the photo-realistic retinal shell 7 is made from a thin sheet of thermal-formable plastic. The photo-realistic retinal image is firstly printed on the flat sheet with a resolution of 1200×1200 dpi or higher. The image resolution can be further increased via a shrinking process after the printing. The photo-realistic retinal shell 7 is preferably a hemisphere with a nominal radius of 7.5 mm for an infant. In such case, imaging the whole periphery edge of the hemisphere corresponds to a 180-degree field of view.

In another preferable embodiment, the photo-realistic retinal features 7b may include representation of retinal pathology associated with retinal diseases, such as retinopathy of prematurity.

Figure 4:
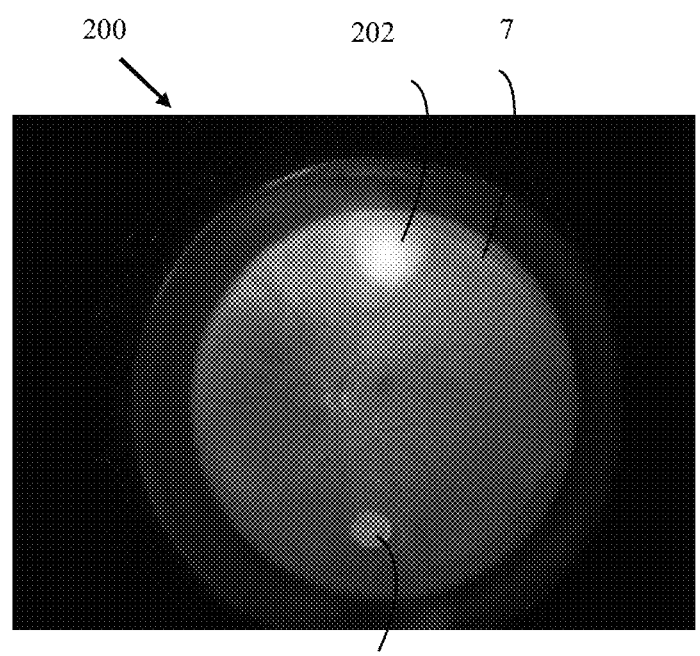
FIG. 4 illustrates an image of a photo-realistic retinal shell, of which the image is taken through an eye model for wide field retinal imaging.

FIG. 4 illustrates a retinal image 200 of a photo-realistic retinal shell 7, of which the image is taken through an eye model 100 for wide field retinal imaging. As shown in retinal image 200, there is a $1^{st}$ Purkinje reflection spot 201 and a $4^{th}$ Purkinje reflection spot 202. These Purkinje spots are anatomically accurate as said spots are in the correct location, of the correct size, and of the correct diffuseness and reflectivity as seen on a human eye.

Figure 5:
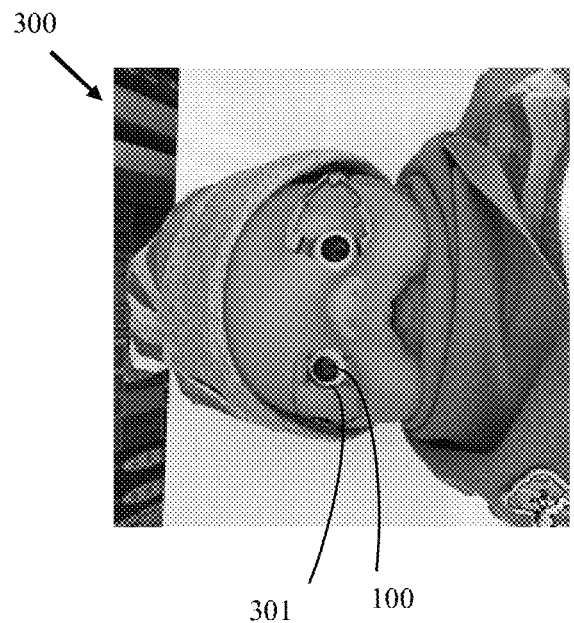
FIG. 5 illustrates a silicon baby simulator with an infant eye model inserted in the left eye.

FIG. 5 illustrates a silicon baby simulator 300 with an infant eye model 100 inserted in its left eye 301. There are commercially available silicon dolls of 16 inches for a premature baby and 18 inches for a full-term baby.

Figure 6:
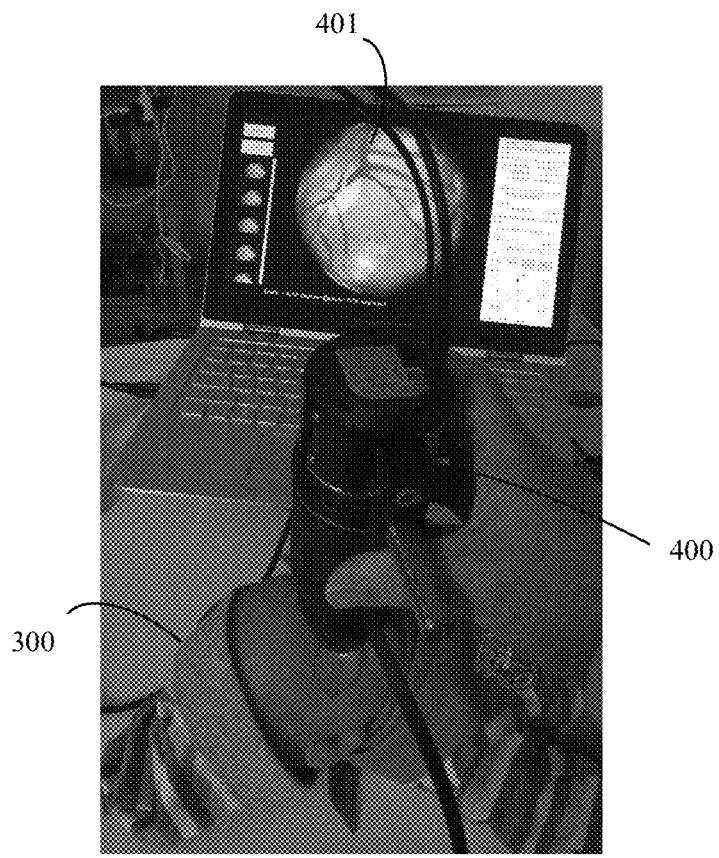
FIG. 6 illustrates a wide field fundus imager taking a retinal image from the silicon baby simulator.

FIG. 6 illustrates a wide field fundus imager 400 taking a retinal image 401 from the silicon baby simulator 300. With proper imaging optics, the wide field fundus imager 400 is capable of taking a retinal image of 160 degrees or greater.

In another preferred embodiment, the above eye model 1 can be made to implement dimensional parameters of adult eyes. For an adult eye model, the anterior surface of corneal model 1 shall have a nominal radius of 8 mm; the outer diameter of the eye model 100 shall have a nominal value of 24 mm; the posterior surface of the lens model 6 shall have a nominal radius of 6.3 mm; and the photorealistic retinal hemisphere 7 shall have a nominal radius of 11 mm.

In an embodiment of a simplified eye model, the posterior surface of corneal model 1 can be merged with the anterior surface of the lens model 6 while the internal spherical chamber 10 is filled with water or clear mineral oil. In another embodiment of a simplified eye model, the posterior surface of corneal model 1 can be merged with the anterior surface of the lens model 6 while the internal spherical chamber 10 is just left empty. In a further embodiment of a simplified eye model, the photo-realistic retinal image can be stamped on the interior wall of the back part 3.

The above description is intended to be illustrative, and not restrictive. It is submitted with the understanding that it will not be used to interpret or limit the scope or meaning of the claims. The scope of the invention should be determined with reference to the appended claims, along with the full scope of equivalents to which such claims are entitled.

What is claimed is:

1. An eye model having a central axis, configured for wide field retinal imaging, comprising:
   a cornea model comprising a translucent plastic and having a convex anterior surface configured to provide a first Purkinje image;
   a lens model comprising a glass or plastic convex-convex lens configured to provide a fourth Purkinje image;
   an iris model disposed between the lens model and the cornea model; and
   a retinal model comprising a retinal shell having a concave retinal surface and a photographic retina image disposed on the concave retinal surface, the eye model being configured to provide a viewable field of at least 80 degrees on the retinal surface measured relative to the central axis,
   wherein a space between the lens model and the retinal model is filled with a transparent liquid, and
   wherein at least one of the cornea model and the lens model comprises a birefringent material.

2. The eye model of claim 1, wherein said cornea model is a cornea model of an infant wherein the convex anterior surface has a nominal radius of curvature of about 6 mm or is a cornea model of an adult wherein the convex anterior surface has a nominal radius of curvature of about 8 mm.

3. The eye model of claim 1, wherein said shell and said photographic retinal image are hemispherical and both have a nominal diameter of about 15 mm corresponding to an infant eye or both have a nominal diameter of about 22 mm corresponding to an adult eye.

4. The eye model of claim 1, wherein said retinal shell is made from a thermal formable material.

5. The eye model of claim 1, wherein said transparent liquid is water.

6. The eye model of claim 1, wherein said cornea model is made of PMMA.

7. The eye model of claim 1, wherein said cornea model is made of lightly translucent acrylic.

8. The eye model of claim 1, wherein the photographic retinal image is an inkjet image.

9. An eye model having a central axis, configured for wide field retinal imaging, comprising:
   an integrated cornea-lens model comprising a convex anterior surface; and
   a retinal model comprising a retinal shell having a concave retinal surface and a photographic retinal image disposed on the concave retinal surface,
   the eye model being configured to provide a viewable field of at least 80 degrees on the retinal surface measured relative to the central axis,
   a watertight enclosure enabling said eye model to be filled with a transparent liquid,
   wherein the cornea-lens model comprises a birefringent material.

10. The eye model of claim 9, wherein said anterior surface of said cornea-lens model has a nominal radius of curvature of approximately 6 mm or has a nominal radius of curvature of approximately 8 mm.

11. The eye model of claim 9, wherein said retinal shell is a hemisphere with a nominal diameter of approximately 15 mm or 22 mm.

12. The eye model of claim 9, wherein said photographic retinal image includes retinal details of a diseased retina.

13. A method for creating an eye model, comprising the steps of:
   providing a cornea model comprising a convex anterior surface configured to provide a first Purkinje image;
   providing a lens model comprising a convex-convex lens configured to provide a fourth Purkinje image;
   providing an iris model disposed between the lens model and the cornea model; and
   producing a retinal model by printing a photographic image of a retina on a thermally-deformable material and, after the step of printing the photographic image, deforming said thermally-deformable material such that retinal model comprises a retinal shell having the photographic image disposed on a curved surface, and
   positioning the retinal shell such that the photographic image can be viewed through the cornea model, the lens model and the iris model.

14. The method of claim 13, further comprising a step of acquiring the photographic image by imaging a human retina using an ophthalmic camera.

15. The method of claim 13, wherein said photographic image of said retina covers an angle of at least 80 degrees in all angular directions relative to a central axis of the eye model.

16. The method of claim 13, wherein said step of deforming is achieved using a vacuum forming molding technique.

17. The method of claim 13, further comprising generating the photographic retinal image by forming a composite image of a plurality of retinal photographic images.

* * * * *